US008906861B2

(12) United States Patent
Tien et al.

(10) Patent No.: US 8,906,861 B2
(45) Date of Patent: Dec. 9, 2014

(54) PHARMACEUTICAL COMPOSITIONS COMPRISING CYCLOSPORINS

(75) Inventors: Walter L. Tien, Irvine, CA (US); Richard S. Graham, Irvine, CA (US); James N. Chang, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 506 days.

(21) Appl. No.: 12/361,335

(22) Filed: Jan. 28, 2009

(65) Prior Publication Data

US 2009/0131307 A1    May 21, 2009

Related U.S. Application Data

(63) Continuation of application No. 11/161,218, filed on Jul. 27, 2005, now Pat. No. 7,501,393.

(51) Int. Cl.
| | | |
|---|---|---|
| A61K 38/13 | (2006.01) | |
| A61K 38/12 | (2006.01) | |
| A61K 9/08 | (2006.01) | |
| C07K 5/12 | (2006.01) | |
| A61K 9/00 | (2006.01) | |

(52) U.S. Cl.
CPC ............... *A61K 38/13* (2013.01); *A61K 9/0048* (2013.01); *A61K 9/0019* (2013.01)
USPC ......... 514/20.5; 514/20.8; 514/199; 604/294; 424/78.04

(58) Field of Classification Search
None
See application file for complete search history.

(56) References Cited

U.S. PATENT DOCUMENTS

| | | | |
|---|---|---|---|
| 4,388,307 A | 6/1983 | Cavanak | |
| 4,649,047 A | 3/1987 | Kaswan | |
| 4,814,323 A | 3/1989 | Andrieu et al. | |
| 4,839,342 A | 6/1989 | Kaswan | |
| 4,996,193 A | 2/1991 | Hewitt et al. | |
| 5,047,396 A | 9/1991 | Orban et al. | |
| 5,051,402 A | 9/1991 | Kurihara et al. | |
| 5,342,625 A | 8/1994 | Hauer et al. | |
| 5,474,979 A * | 12/1995 | Ding et al. ...................... 514/11 |
| 5,543,393 A | 8/1996 | Kim et al. | |
| 5,614,491 A | 3/1997 | Walch et al. | |
| 5,639,724 A | 6/1997 | Cavanak | |
| 5,652,212 A | 7/1997 | Cavanak et al. | |
| 5,759,997 A | 6/1998 | Cavanak | |
| 5,766,629 A | 6/1998 | Cho et al. | |
| 5,798,333 A | 8/1998 | Sherman | |
| 5,827,822 A | 10/1998 | Floc'h et al. | |
| 5,834,017 A | 11/1998 | Cho et al. | |
| 5,891,846 A | 4/1999 | Ishida et al. | |
| 5,916,589 A | 6/1999 | Hauer et al. | |
| 5,951,971 A | 9/1999 | Kawashima et al. | |
| 5,962,014 A | 10/1999 | Hauer et al. | |
| 5,962,017 A | 10/1999 | Hauer et al. | |
| 5,962,019 A | 10/1999 | Cho et al. | |
| 5,977,066 A | 11/1999 | Cavanak | |
| 6,007,840 A | 12/1999 | Hauer et al. | |
| 6,024,978 A | 2/2000 | Hauer et al. | |
| 6,057,289 A | 5/2000 | Mulye | |
| 6,197,335 B1 | 3/2001 | Sherman | |
| 6,254,860 B1 | 7/2001 | Garst | |
| 6,254,885 B1 | 7/2001 | Cho et al. | |
| 6,267,985 B1 | 7/2001 | Chen et al. | |
| 6,284,268 B1 | 9/2001 | Mishra et al. | |
| 6,294,192 B1 | 9/2001 | Patel et al. | |
| 6,306,825 B1 | 10/2001 | Cavanak | |
| 6,350,442 B2 | 2/2002 | Garst | |
| 6,468,968 B2 | 10/2002 | Cavanak et al. | |
| 6,475,519 B1 | 11/2002 | Meinzer et al. | |
| 6,486,124 B2 | 11/2002 | Olbrich et al. | |
| 6,569,463 B2 | 5/2003 | Patel et al. | |
| 6,582,718 B2 * | 6/2003 | Kawashima et al. ......... 424/427 |
| 6,638,522 B1 | 10/2003 | Mulye | |
| 6,656,504 B1 | 12/2003 | Bosch et al. | |
| 6,677,304 B2 | 1/2004 | Di Napoli | |
| 6,723,339 B2 | 4/2004 | Meinzer et al. | |
| 6,916,785 B2 | 7/2005 | Patel | |
| 7,501,393 B2 * | 3/2009 | Tien et al. ........................ 514/11 |
| 2001/0003589 A1 | 6/2001 | Neuer et al. | |
| 2001/0036449 A1 | 11/2001 | Garst | |
| 2002/0012680 A1 | 1/2002 | Patel et al. | |
| 2002/0013272 A1 | 1/2002 | Cavanak et al. | |
| 2002/0016290 A1 | 2/2002 | Floc'h et al. | |
| 2002/0016292 A1 | 2/2002 | Richter et al. | |
| 2002/0025927 A1 | 2/2002 | Olbrich et al. | |
| 2002/0045601 A1 | 4/2002 | Kawashima et al. | |
| 2002/0107183 A1 | 8/2002 | Petswzulat et al. | |
| 2002/0119190 A1 | 8/2002 | Meinzer et al. | |
| 2002/0165134 A1 | 11/2002 | Richter et al. | |
| 2003/0060402 A1 | 3/2003 | Cavanak et al. | |
| 2003/0133984 A1 | 7/2003 | Ambuhl et al. | |
| 2003/0143250 A1 | 7/2003 | Hauer et al. | |
| 2003/0147954 A1 | 8/2003 | Yang et al. | |
| 2003/0166517 A1 | 9/2003 | Fricker et al. | |
| 2003/0211983 A1 | 11/2003 | Petszulat et al. | |

(Continued)

FOREIGN PATENT DOCUMENTS

| | | |
|---|---|---|
| EP | 0471293 | 2/1992 |
| EP | 0547229 | 6/1992 |
| WO | WO 00/00179 | 1/2000 |
| WO | WO 01/32142 | 5/2001 |

OTHER PUBLICATIONS

Retrieved from: http://home.nas.net/~dbc/cic_hamilton/dictionary/s.html , 4 pages, 2009 [Retrieved on Nov. 19, 2009].*

(Continued)

*Primary Examiner* — Satyanarayana R Gudibande
(74) *Attorney, Agent, or Firm* — Laura L. Wine; Joel B. German; Debra D. Condino

(57) ABSTRACT

A composition is described herein comprising cyclosporin A, polysorbate 80, a polyoxyethylene stearate, and an oil; wherein the composition is an emulsion which is ophthalmically acceptable. Methods of treating diseases or conditions using said compositions, and medicaments related thereto, are also disclosed herein.

9 Claims, No Drawings

(56) References Cited

U.S. PATENT DOCUMENTS

| | | |
|---|---|---|
| 2003/0215496 A1 | 11/2003 | Patel et al. |
| 2004/0048789 A1 | 3/2004 | Patel |
| 2004/0101552 A1 | 5/2004 | Patel |
| 2004/0102366 A1 | 5/2004 | Patel |
| 2004/0106546 A1 | 6/2004 | Napoli |
| 2004/0161458 A1 | 8/2004 | Meinzer et al. |
| 2004/0167063 A1 | 8/2004 | Cavanak et al. |
| 2004/0191284 A1* | 9/2004 | Yu et al. ................. 424/401 |
| 2004/0198645 A1 | 10/2004 | Ambuhl et al. |
| 2005/0048087 A1 | 3/2005 | Posanski |
| 2005/0059583 A1 | 3/2005 | Acheampong et al. |
| 2005/0118254 A1 | 6/2005 | Choi et al. |
| 2005/0129718 A1 | 6/2005 | Sherman |
| 2005/0147659 A1 | 7/2005 | Carli et al. |

OTHER PUBLICATIONS

Kuwano et al, "Cyclosporine A Formulation Affects Its Ocular Distribution in Rabbits", Pharmaceutical Research, vol. 19, No. 1, Jan. 2002, 108-111.

Kaur, 1979, Journal of Pharmacy and Pharmacology, 31, 48P (2 pages).

* cited by examiner

PHARMACEUTICAL COMPOSITIONS COMPRISING CYCLOSPORINS

RELATED APPLICATION

This application claims the benefit of priority under 35 U.S.C. §120 of U.S. application Ser. No. 11/161,218 filed on Jul. 27, 2005, the disclosure of which is hereby incorporated in its entirety herein by reference.

A composition is described herein comprising cyclosporin A, polysorbate 80, a polyoxyethylene stearate, and an oil; wherein the composition is an emulsion which is ophthalmically acceptable.

A therapeutically effective concentration of cyclosporin is a concentration useful to observe a therapeutic effect as compared to a placebo composition having the same composition sans cyclosporin, and can be determined by a person of ordinary skill in the art without undue experimentation. In one embodiment the cyclosporin concentration is 0.001% or greater. In other embodiments, the concentration of cyclosporin is greater than 0.01%. In other embodiments, the concentration of cyclosporin is greater than 0.02%. In other embodiments, the concentration of cyclosporin is at least 0.05%. For the treatment of dry eye disease, a cyclosporin concentration of less than or equal to 1% is often adequate. In other words, in certain compositions, the concentration of the cyclosporin is at or below 1%. In other embodiments, the concentration of cyclosporin is at or below 0.2%. In other embodiments, the concentration of cyclosporin is at or below 0.15%. In other embodiments, the concentration of cyclosporin is at or below 2%. In other embodiments, the concentration of cyclosporin is about 0.05%. In other embodiments, the concentration of cyclosporin is about 0.1%.

A polyoxyethylene stearate is an ester of polyoxyethylene $HO(-CH_2CH_2O)_n-OH$ and stearic acid. Such esters include, but are not limited to the following, where the average number for n is indicated as polyoxyethylene n stearate: polyoxyethylene 6 stearate, polyoxyethylene 8 stearate, polyoxyethylene 12 stearate, polyoxyethylene 20 stearate, polyoxyethylene 40 stearate, polyoxyethylene 50 stearate, and polyoxyethylene 100 stearate. Distearates may also be used.

The concentration of the polyoxyethylene stearate may vary. In one embodiment, the concentration of polyoxyethylene stearate is from 0.01% to 20%. In another embodiment, the concentration of polyoxyethylene stearate is from 0.01% to 10%. In another embodiment, the concentration of polyoxyethylene stearate is from 0.01 to 5.0%.

In one embodiment, the polyoxyethylene stearate is polyoxyethylene 40 stearate. In one embodiment, the concentration of polyoxyethylene 40 stearate is from 0.01% to 20%. In another embodiment, the concentration of polyoxyethylene 40 stearate is from 0.01% to 10%. In another embodiment, the concentration of polyoxyethylene 40 stearate is from 0.01 to 5.0%.

The concentration of polysorbate 80 may vary. In one embodiment, the concentration of polysorbate 80 is from 0.01% to 12%. In another embodiment, the concentration of polysorbate 80 is from 0.01% to 5.0%. In another embodiment, the concentration of polysorbate 80 is from 0.01% to 3.0%.

An oil is a hydrophobic and lipophilic liquid. In other words, it dissolves lipophilic materials, but is substantially insoluble in water. The term oil as applied herein means a single oil or a blend thereof unless otherwise indicated. There are a number of different oils which are suitable for preparing the emulsions disclosed herein. These are known to those of ordinary skill in the art.

While not a necessary consideration, the specific gravity may be important to the stability of the emulsion. Certain embodiments use an oil having a specific gravity of from about 0.9 to about 1.1. Other embodiments use an oil having a specific gravity of from about 0.95 to about 1.1. Other embodiments us an oil having a specific gravity of about 1. A combination of oils may be used to tune the specific gravity as desired.

Oils having a specific gravity of from 0.95 to 1.1 include anise oil, castor oil, clove oil, cassia oil, cinnamon oil, and the like. Oils having a specific gravity of from 0.90 to 0.95 include almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalpytus oil, sesame oil, and the like.

One embodiment comprises an oil having a specific gravity from 0.95 to 1.1.

Another embodiment comprises Anise oil.
Another embodiment comprises Castor oil.
Another embodiment comprises Clove oil.
Another embodiment comprises Cassia oil.
Another embodiment comprises Cinnamon oil.
Another embodiment comprises an oil having a specific gravity between 0.90 and 0.95.
Another embodiment comprises Almond oil.
Another embodiment comprises Corn oil.
Another embodiment comprises Arachis oil.
Another embodiment comprises Cottonseed oil.
Another embodiment comprises Safflower oil.
Another embodiment comprises Maize oil.
Another embodiment comprises Linseed oil.
Another embodiment comprises Rapeseed oil.
Another embodiment comprises Soybean oil.
Another embodiment comprises Olive oil.
Another embodiment comprises Caraway oil.
Another embodiment comprises Rosemary oil.
Another embodiment comprises Peanut oil.
Another embodiment comprises Peppermint oil.
Another embodiment comprises Sunflower oil.
Another embodiment comprises Eucalpytus oil.
Another embodiment comprises Sesame oil.
Another embodiment comprises an oil having a specific gravity below 0.9.
Another embodiment comprises Mineral oil.
Another embodiment comprises Coriander oil.
Another embodiment comprises Lavender oil.
Another embodiment comprises Citronella oil.
Another embodiment comprises Juniper oil.
Another embodiment comprises Lemon oil.
Another embodiment comprises Orange oil.
Another embodiment comprises Clary sage oil.
Another embodiment comprises Nutmeg oil.
Another embodiment comprises Tea tree oil.

The amount of oil may vary depending upon the circumstances. In one embodiment, the amount of oil is from 0.01% to 10%. In another embodiment, the amount of oil is from 0.01% to 5.0%. In another embodiment, the amount of oil is from 0.01% to 3.0%.

One embodiment comprises from 0.01% to 10% castor oil. Another embodiment comprises from 0.01% to 5.0% castor oil. Another embodiment comprises from 0.01% to 3.0% castor oil.

Unless otherwise indicated, all uses of % in the specification and the claims herein are intended to mean % (weight/weight).

A liquid which is intended for ophthalmic use or ophthalmically acceptable is formulated such that it can be administered topically to the eye. The comfort should be maximized as much as possible, although sometimes formulation considerations may necessitate less than optimal comfort. In the case that comfort cannot be maximized, the liquid should be formulated such that the liquid is tolerable to the patient for topical ophthalmic use. Additionally, an ophthalmically acceptable liquid may be packaged for single use, or contain a preservative to prevent contamination over multiple uses.

As is known in the art, buffers are commonly used to adjust the pH to a desirable range for ophthalmic use. Generally, a pH of around 5-8 is desired, however, this may need to be adjusted due to considerations such as the stability or solubility of the therapeutically active agent or other excipients. Many buffers including salts of inorganic acids such as phosphate, borate, and sulfate are known.

Another commonly used excipient in ophthalmic compositions is a viscosity-enhancing, or a thickening agent. Thickening agents may be used for a variety of reasons, ranging from improving the form of the formulation for convenient administration to improving the contact with the eye to improve bioavailability. The thickening agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful thickening agents are sodium carboxymethylcellulose, hydroxypropylmethylcellulose, povidone, polyvinyl alcohol, and polyethylene glycol.

In ophthalmic solutions, tonicity agents may be used to adjust the composition of the formulation to the desired isotonic range. Tonicity agents are well known in the art and some examples include glycerin, mannitol, sorbitol, sodium chloride, and other electrolytes.

Preservatives may be used to prevent bacterial contamination in multiple-use ophthalmic preparations. Preservatives are well known in the art, and, while not intending to be limiting, examples include polyhexamethylenebiguanidine (PHMB), benzalkonium chloride (BAK), stabilized oxychloro complexes (otherwise known as Purite®), phenylmercuric acetate, chlorobutanol, benzyl alcohol, parabens, and thimerosal are examples of useful preservatives.

In ophthalmic compositions, a chelating agent may be used to enhance preservative effectiveness. Suitable chelating agents are those known in the art, and, while not intending to be limiting, edetate (EDTA) salts like edetate disodium, edetate calcium disodium, edetate sodium, edetate trisodium, and edetate dipotassium are examples of useful chelating agents.

The compositions disclosed herein are useful in the treatment of dry eye disease, and in the preparation of medicaments for the treatment of dry eye disease. However, certain compositions disclosed herein are also useful for the treatment or prevention of other conditions or diseases which are related to immune response, inflammatory response, or parasitic or other infection.

The compositions disclosed herein are also useful for parenteral administration of a cyclosporin. A composition which is formulated for parenteral use is a composition which is formulated with the intention of administering the composition parenterally. Parenteral administration is generally characterized by injection, either subcutaneously, intramuscularly or intravenously.

The best mode of making and using the present invention are described in the following examples. These examples are given only to provide direction and guidance in how to make and use the invention, and are not intended to limit the scope of the invention in any way.

EXAMPLE 1

An emulsion having the composition in the table below was prepared as described below.

Part I

CsA (0.5 gm) was added to 50 ml of 10% POE-40 S stock solution. The mixture was stirred for about 20 minutes at room temperature until most of CsA was dissolved in the POE-40-S solution. Castor oil (1 gm) was added and stirred another 15 minutes at room temperature. CMC stock solution (5%, 50 mL) was added and stirred about 20 minutes at room temperature.

Part II

Polysorbate 80 (1.0 gm) was added to water (~380 mL) and stirred at room temperature until dissolved. Glycerine (5.0 g) was added and the mixture was stirred at room temperature until the glycerine was dissolved. Boric acid (3.0 g) was then added to the solution, and stirred at room temperature until dissolved.

Part I and Part II were mixed for about 30 minutes, and the pH was adjusted to pH 7.3 using NaOH (1.0 N, ~3 ml). The mixture was heated to 60° C. with mixing in a closed system to prevent water loss, homogenized at 12,000 rpm at 60° C. for 15 minutes, and cooled to room temperature. Purite (2.26 g, 2.2196) was added to the emulsion and mixed well, water was added to the mixture to make 500 ml, and the emulsion was thoroughly mixed. Finally, the emulsion was sterile filtered using a 0.22 um filter.

| Ingredients | |
|---|---|
| Cyclosporin A (w/w %) | 0.1 |
| Castor Oil (w/w %) | 0.20 |
| Polyoxyethylene 40 Sterate (Myrj 52) | 0.75 |
| Polysorbate 80 (w/w %) | 0.20 |
| Glycerin (w/w %) | 1.00 |
| Boric Acid (w/w %) | 0.60 |
| CMC—Carboxymethyl Cellulose (low viscosity) (w/w %) | 0.5 |
| Purite (ppm) | 100.0 ppm |
| Purified Water | QS |
| Sodium Hydroxide | pH adjustment |
| pH | pH = 7.3-7.5 |

EXAMPLE 2

An emulsion having the composition in the table below was prepared as described below.

Part I

CsA (0.5 gm) was added to 2.5 gm of Castor oil. The mixture was stirred for about 20 minutes at room temperature until most of CsA was dissolved in the Castor oil. 50 ml of 10% POE-40 S stock solution was added to above mixture and stirred another 15 minutes at room temperature. 2.5 gm of Polysorbate-80 was added and stirred about 20 minutes at room temperature.

Part II

Glycerine (7.0 g) was added to water (~380 mL) and stirred at room temperature until the glycerine was dissolved. Boric acid (3.0 g) was then added to the solution, and stirred at room temperature until dissolved. CMC stock solution (5%, 50 mL) was added and the mixture was stirred at room temperature for another 20 minutes.

Part I and Part II were mixed for about 30 minutes, and the pH was adjusted to pH 7.3 using NaOH (1.0 N, ~3 ml). The mixture was heated to 60° C. with mixing in a closed system to prevent water loss, homogenized at 12,000 rpm at 60° C. for 20 minutes, and cooled to room temperature. Purite (2.26 g, 2.21%) was added to the emulsion and mixed well, water was added to the mixture to make 500 ml, and the emulsion was thoroughly mixed. Finally, the emulsion was sterile filtered using a 0.22 um filter.

| Ingredients | |
|---|---|
| Cyclosporin A (w/w %) | 0.1 |
| Castor Oil (w/w %) | 0.50 |
| Polyoxyethylene 40 Sterate (Myrj 52) | 1.0 |
| Polysorbate 80 (w/w %) | 0.50 |
| Glycerin (w/w %) | 1.40 |
| Boric Acid (w/w %) | 0.60 |
| CMC—Carboxymethyl Cellulose (low viscosity) (w/w %) | 0.5 |
| Purite (ppm) | 100.0 ppm |
| Purified Water | QS |
| Sodium Hydroxide | pH adjustment |
| pH | pH = 7.3-7.5 |

EXAMPLE 3

Dry eye is treated using a composition of Example 1 or 2. Relief of symptoms is experienced.

What is claimed is:

1. A composition comprising cyclosporine A in a concentration of 0.001% to 0.005% w/v, polysorbate 80, sodium carboxymethylcellulose, mannitol, glycerine and a preservative wherein the composition is a solution which is ophthalmically acceptable.

2. The composition of claim 1 wherein the preservative is an oxychloro compound.

3. The composition of claim 1 wherein polysorbate 80 is present in an amount of 1.0% w/v.

4. The composition of claim 1 wherein the sodium carboxymethylcellulose is present in an amount of 0.5% w/v.

5. The composition of claim 4 further comprising sodium citrate dehydrate.

6. The composition of claim 5, wherein glycerine is present in the amount of 1.0% w/v.

7. The composition of claim 6 further comprising boric acid.

8. The composition of claim 6 further comprising Pemulen.

9. A composition consisting essentially of cyclosporine A in a concentration of 0.001% to 0.005% w/v, polysorbate 80, sodium carboxymethylcellulose, mannitol, glycerine and a preservative wherein the composition is a solution which is ophthalmically acceptable.

* * * * *